(12) United States Patent
McGown

(10) Patent No.: US 8,932,306 B1
(45) Date of Patent: Jan. 13, 2015

(54) DEVICE AND ASSOCIATED METHOD FOR USE IN THE TREATMENT OF HEMORRHOIDS

(76) Inventor: George Percy McGown, Brooklyn, NY (US)

(*) Notice: Subject to any disclaimer, the term of this patent is extended or adjusted under 35 U.S.C. 154(b) by 1946 days.

(21) Appl. No.: 12/012,824

(22) Filed: Feb. 6, 2008

(51) Int. Cl.
A61B 17/10 (2006.01)

(52) U.S. Cl.
USPC ........................................ 606/140

(58) Field of Classification Search
USPC ............... 606/139, 140, 232; 29/235; 100/9; 433/3, 8, 15, 7, 23
See application file for complete search history.

(56) References Cited

U.S. PATENT DOCUMENTS

| | | | | |
|---|---|---|---|---|
| 2,764,160 A * | 9/1956 | Alexander et al. | ............. | 606/140 |
| 3,726,278 A * | 4/1973 | Scott | ............. | 606/163 |
| 3,815,243 A * | 6/1974 | Eames | ............. | 433/149 |
| 4,257,419 A * | 3/1981 | Goltner et al. | ............. | 606/140 |
| 4,548,201 A * | 10/1985 | Yoon | ............. | 606/141 |
| 4,696,646 A * | 9/1987 | Maitland | ............. | 433/149 |
| 4,794,927 A * | 1/1989 | Yoon | ............. | 606/140 |
| 5,083,556 A * | 1/1992 | Osbon et al. | ............. | 600/39 |
| 5,203,863 A * | 4/1993 | Bidoia | ............. | 606/140 |
| 5,643,290 A * | 7/1997 | Clark et al. | ............. | 606/141 |
| 5,741,273 A * | 4/1998 | O'Regan | ............. | 606/140 |
| 6,001,100 A * | 12/1999 | Sherman et al. | ............. | 606/232 |
| 6,379,361 B1 * | 4/2002 | Beck et al. | ............. | 606/323 |
| 6,482,213 B1 * | 11/2002 | Riza | ............. | 606/140 |
| 6,761,562 B2 * | 7/2004 | Von Weissenfluh | ............. | 433/149 |
| 6,974,466 B2 * | 12/2005 | Ahmed et al. | ............. | 606/140 |
| 7,223,101 B2 * | 5/2007 | Garrison et al. | ............. | 433/149 |

* cited by examiner

Primary Examiner — Dianne Dornbusch
Assistant Examiner — Alexander Orkin
(74) Attorney, Agent, or Firm — R. Neil Sudol; Henry D. Coleman

(57) ABSTRACT

A medical device for use in hemorrhoid treatment is an elongate unitary body having a conical portion at one end and a cylindrical portion at an opposite end. The cylindrical portion is truncated along a longitudinal plane to provide the cylindrical portion with a planar outer surface area extending parallel to a longitudinal axis of the body. A coupling structure is provided on a side of the cylindrical portion opposite the conical portion for releasably attaching the body to a band-holding cylinder of a hemorrhoid ligator.

20 Claims, 1 Drawing Sheet

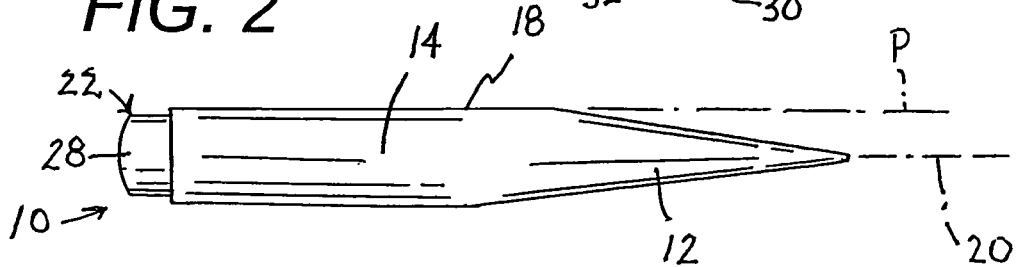
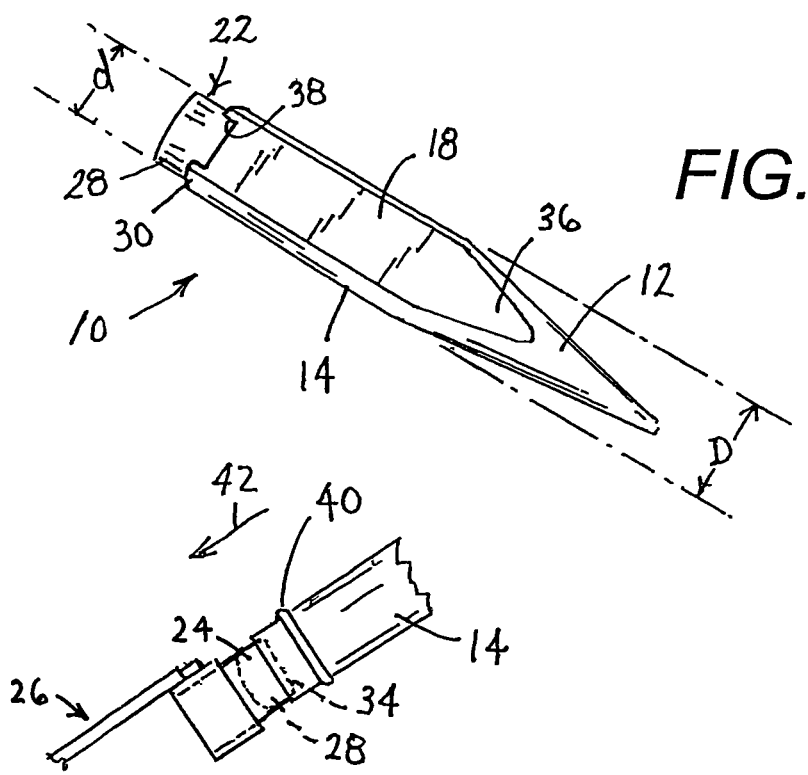

DEVICE AND ASSOCIATED METHOD FOR USE IN THE TREATMENT OF HEMORRHOIDS

BACKGROUND OF THE INVENTION

This invention relates to a medical device useful in the treatment of hemorrhoids. More particularly, this invention relates to a medical device useful in the treatment of hemorrhoids by ligation. Even more particularly, this invention relates to a hemorrhoidal band installation device for use by doctors and colorectal surgeons for the treatment of hemorrhoids It is a well-established medical procedure to place an elastic band about a hemorrhoid to cut off the blood supply to the hemorrhoid thereby resulting in necrosis of the hemorrhoidal tissues. The elastic band is initially disposed around a metal cylinder at the distal end of a ligator. The physician draws the hemorrhoid into the cylinder by inserting the jaws of a forceps through the cylinder and manipulating the forceps to grasp the hemorrhoid and pull it into the cylinder. Operating an actuator at the handle end of the ligator, the physician shifts a second cylinder in a distal direction over the first cylinder, thereby pushing the elastic band off of the first cylinder and onto the hemorrhoid.

It can be difficult to place the elastic band in a stretched condition over the distal end of the metal cylinder. The loading process may be facilitated through the use of a loading cone. The loading cone has a conical portion at one end and a cylindrical portion at the other end. The free end of the cylindrical portion, opposite the conical portion, is removably attachable to the inner metal cylinder at the distal end of the ligator. The user places an elastic band about the pointed end of the loading cone and rolls the band "up" the conical portion onto the cylindrical portion. The loading cone may then be attached to the ligator, whereupon one rolls the band further along the cylindrical portion of the loading cone and onto the metal band-holding cylinder of the ligator. The loading cone is removed from the loaded ligator and the user, typically a doctor or other medical professional, manipulates the ligator in a hemorrhoid treatment procedure wherein the band is placed about a hemorrhoid.

OBJECTS OF THE INVENTION

It is an object of the present invention to provide an improved loading cone for positioning an elastic hemorrhoid ligation band in a stretched configuration over a metal band-holding cylinder of a ligator.

This and other objects of the present invention will be apparent from the drawings and descriptions herein. Although every object of the invention is believed to be attained in at least one embodiment of the invention, there is not necessary any single embodiment that achieves all of the objects of the invention.

SUMMARY OF THE INVENTION

A medical device for use in hemorrhoid treatment comprises, in accordance with the present invention, an elongate body having a conical portion at one end and a cylindrical portion at an opposite end, the cylindrical portion being truncated along a longitudinal plane to provide the cylindrical portion with a planar outer surface area extending parallel to a longitudinal axis of the body. A coupling structure is provided on a side of the cylindrical portion opposite the conical portion for releasably attaching the body to a band-holding cylinder of a hemorrhoid ligator.

Where the cylindrical portion has a major transverse dimension or diameter, the coupling structure may include a cylindrical projection extending axially from the cylindrical portion opposite the conical portion, the projection having a diameter smaller than the major transverse dimension or diameter of the cylindrical portion. The projection is removably insertable into the band-holding cylinder of the ligator. The coupling structure may further include a flange extending axially from the cylindrical portion, the flange being radially spaced from the projection to define therewith a groove for receiving a distal circular edge of the band-holding cylinder of the ligator.

Pursuant to further features of the present invention, the planar outer surface area is rectangular and includes at one end a tapered triangular area extending along part of the conical portion and at an opposite end a rectangular cutout. The cutout also interrupts the flange so that the flange takes the form of a slotted ring.

A loading cone in accordance with the present invention facilitates the ligator-loading procedure. It becomes easier to slide or roll the band along the cylindrical portion of the loading cone and onto the ligator's band-holding cylinder. The user places a finger or thumb into contact with the band over the flat or land area of the cone and pushes the band away from the conical end of the device.

BRIEF DESCRIPTION OF THE DRAWINGS

FIG. 1 is a schematic perspective view of a band-loading cone in accordance with the present invention, for use in hemorrhoid treatment procedures.

FIG. 2 is a side elevational view of the loading cone of FIG. 1.

FIG. 3 is an end elevational view of the loading cone of FIGS. 1 and 2, taken from the left hand side in FIG. 2.

FIG. 4 is a partial side elevational view of the loading cone of FIGS. 1-3, showing use of the cone to place an elastic band about a dispensing cylinder of a hemorrhoid ligator.

DETAILED DESCRIPTION

As illustrated in FIGS. 1-3, a medical device for use in hemorrhoid treatment comprises an elongate unitary body 10 having a conical portion 12 at one end and a cylindrical portion 14 at an opposite end, the conical portion and the cylindrical portion being integral and continuous with one another. Cylindrical portion 14 is truncated along a longitudinal plane P to provide the cylindrical portion with a planar outer surface area 18 extending parallel to a longitudinal axis 20 of body 10. A coupling structure 22 is provided on a side of cylindrical portion 14 opposite conical portion 12 for releasably attaching body 10 to a band-holding and -dispensing cylinder 24 (FIG. 4) of a hemorrhoid ligator 26.

Cylindrical portion 14 has a major transverse dimension or diameter D. Coupling structure 22 includes a cylindrical projection 28 extending axially from cylindrical portion 14 opposite conical portion 12. Projection 28 has a diameter d smaller than the major transverse dimension or diameter D of cylindrical portion 14. Projection 28 is removably insertable into the band-holding and -dispensing cylinder 24 of ligator 26. Coupling structure 22 further includes a flange 30 extending axially from cylindrical portion 14. Flange 30 is radially spaced from projection 28 to define therewith a circular groove 32 for receiving a distal circular edge 34 of band-holding and -dispensing cylinder 24 of ligator 26.

Planar outer surface area 18 is a rectangular flat or land and includes at one end a tapered triangular area 36 extending along part of conical portion 12 and at an opposite end a rectangular cutout 38. Cutout 38 also interrupts flange 30 so that the flange takes the form of a slotted ring. Planar outer surface or flat 18 has a width larger than the radius D/2 of cylindrical portion 14. Planar outer surface area or flat 18 forms a contact surface for a ligation band wherein a user's finger or thumb contacts the ligation band over the planar outer surface or flat to push the ligation band away from conical portion 12.

During a ligator-loading procedure, one slides or rolls an elastic band 40 first up conical portion 12 to cylindrical portion 14 and then along the cylindrical portion onto band-holding cylinder 26 of ligator 28. The user places a finger or thumb into contact with band 40 over the flat or land area 18 of the cone body 10 and pushes the band away from the conical end of the device towards the ligator 28, as indicated by an arrow 42.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical device comprising an elongate body having a conical portion at one end and a cylindrical portion at an opposite end, said cylindrical portion being truncated along a longitudinal plane to provide said cylindrical portion with a planar outer surface area or flat extending parallel to a longitudinal axis of said body, said planar outer surface area or flat forming a contact surface for a ligation band wherein a user's finger or thumb contacts the ligation band over said planar outer surface or flat to push said ligation band away from said conical portion, a coupling structure being provided on a side of said cylindrical portion opposite said conical portion for releasably attaching said body to a band-holding cylinder of a hemorrhoid ligator.

2. The medical device defined in claim 1 wherein said cylindrical portion has a major transverse dimension or diameter, said coupling structure including a cylindrical projection extending axially from said cylindrical portion opposite said conical portion, said projection having a diameter smaller than the major transverse dimension or diameter of said cylindrical portion, said projection being removably insertable into the band-holding cylinder of the ligator.

3. The medical device defined in claim 2 wherein said coupling structure further includes a flange extending axially from said cylindrical portion, said flange being radially spaced from said projection to define therewith a groove for receiving a distal circular edge of the band-holding cylinder of the ligator.

4. The medical device defined in claim 3 wherein said planar outer surface area or flat is rectangular and includes at one end a tapered triangular area extending along part of said conical portion and at an opposite end a rectangular cutout, said cutout interrupting said flange so that said flange takes the form of a slotted ring.

5. The medical device defined in claim 4 wherein said planar outer surface area or flat includes at one end a tapered triangular area extending along part of said conical portion.

6. The medical device defined in claim 4 wherein said planar outer surface area or flat has a rectangular cutout at an end opposite said conical portion, said cutout interrupting said flange so that said flange takes the form of a slotted ring.

7. The medical device defined in claim 1 wherein said planar outer surface area or flat is substantially rectangular and includes at one end a tapered triangular area extending along part of said conical portion and at an opposite end a rectangular cutout.

8. The medical device defined in claim 1 wherein said planar outer surface area or flat includes at one end a tapered triangular area extending along part of said conical portion.

9. The medical device defined in claim 1 wherein said planar outer surface area or flat has a rectangular cutout at an end opposite said conical portion.

10. A medical device comprising an elongate body having a conical portion at one end and a cylindrical portion at an opposite end, said cylindrical portion being truncated along a longitudinal plane to provide said cylindrical portion with a planar outer surface area or flat extending parallel to a longitudinal axis of said body, said cylindrical portion having a radius, said planar outer surface area or flat having a width larger than said radius, coupling structure being provided on a side of said cylindrical portion opposite said conical portion for releasably attaching said body to a band-holding cylinder of a hemorrhoid ligator.

11. The medical device defined in claim 10 wherein said cylindrical portion has a major transverse dimension or diameter twice said radius, said coupling structure including a cylindrical projection extending axially from said cylindrical portion opposite said conical portion, said projection having a diameter smaller than the major transverse dimension or diameter of said cylindrical portion, said projection being removably insertable into the band-holding cylinder of the ligator.

12. The medical device defined in claim 11 wherein said coupling structure further includes a flange extending axially from said cylindrical portion, said flange being radially spaced from said projection to define therewith a groove for receiving a distal circular edge of the band-holding cylinder of the ligator.

13. The medical device defined in claim 12 wherein said planar outer surface area or flat is rectangular and includes at one end a tapered triangular area extending along part of said conical portion and at an opposite end a rectangular cutout, said cutout interrupting said flange so that said flange takes the form of a slotted ring.

14. The medical device defined in claim 13 wherein said planar outer surface area or flat includes at one end a tapered triangular area extending along part of said conical portion.

15. The medical device defined in claim 13 wherein said planar outer surface area or flat has a rectangular cutout at an end opposite said conical portion, said cutout interrupting said flange so that said flange takes the form of a slotted ring.

16. The medical device defined in claim 10 wherein said planar outer surface area or flat is substantially rectangular and includes at one end a tapered triangular area extending along part of said conical portion and at an opposite end a rectangular cutout.

17. The medical device defined in claim 10 wherein said planar outer surface area or flat includes at one end a tapered triangular area extending along part of said conical portion.

18. The medical device defined in claim 10 wherein said planar outer surface area or flat has a rectangular cutout at an end opposite said conical portion.

19. A medical method comprising: providing an elongate body having a conical portion at one end and a cylindrical portion at an opposite end, said cylindrical portion being truncated along a longitudinal plane to provide said cylindrical portion with a planar outer surface area or flat extending parallel to a longitudinal axis of said body; releasably attaching said body to a band-holding cylinder of a hemorrhoid ligator via a coupling structure provided on a side of said cylindrical portion opposite said conical portion; contacting a ligation band over said planar outer surface or flat with a finger or thumb to push said ligation band away from said conical portion along said cylindrical portion.

20. The medical method defined in claim 19 wherein said cylindrical portion has a major transverse dimension or diameter, said coupling structure including a cylindrical projection extending axially from said cylindrical portion opposite said conical portion, said projection having a diameter smaller than the major transverse dimension or diameter of said cylindrical portion, the releasable attaching of said body to said band-holding cylinder including removably inserting said projection into said band-holding cylinder.

* * * * *